(12) United States Patent
Al-Humam et al.

(10) Patent No.: US 11,739,011 B2
(45) Date of Patent: Aug. 29, 2023

(54) SYSTEMS AND METHODS FOR TESTING BIOCIDE

(71) Applicant: Saudi Arabian Oil Company, Dhahran (SA)

(72) Inventors: Abdulmohsen A. Al-Humam, Dammam (SA); Othman A. Olayan, Al-Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 624 days.

(21) Appl. No.: 16/926,963

(22) Filed: Jul. 13, 2020

(65) Prior Publication Data

US 2022/0009805 A1 Jan. 13, 2022

(51) Int. Cl.
*C02F 1/50* (2023.01)
*A01N 63/00* (2020.01)
*C02F 1/00* (2023.01)

(52) U.S. Cl.
CPC .............. *C02F 1/50* (2013.01); *A01N 63/00* (2013.01); *C02F 1/006* (2013.01)

(58) Field of Classification Search
None
See application file for complete search history.

(56) References Cited

U.S. PATENT DOCUMENTS

| | | | |
|---|---|---|---|
| 6,361,963 B1 | 3/2002 | Smith et al. | |
| 9,739,694 B2 * | 8/2017 | Amanullah | C09K 8/03 |
| 10,478,754 B2 * | 11/2019 | Sehsah | B01D 19/0031 |
| 10,722,819 B2 * | 7/2020 | Sehsah | G05D 7/0658 |
| 11,385,171 B2 * | 7/2022 | Zhu | G01N 21/78 |
| 2007/0142234 A1 * | 6/2007 | Mueller | C09K 8/36 507/203 |

(Continued)

FOREIGN PATENT DOCUMENTS

JP 2020024144 2/2020

OTHER PUBLICATIONS

PCT International Invitation to Pay Additional Fees and Where Applicable, Protest Fees in International Appln. No. PCT/US2021/041241, dated Oct. 26, 2021, 10 pages.

(Continued)

*Primary Examiner* — John J Figueroa
(74) *Attorney, Agent, or Firm* — Fish & Richardson P.C.

(57) ABSTRACT

A biocide testing system includes test columns, a bypass tube, control valves, and a control system. Each test column includes biocide test coupons. The bypass tube is fluidly coupled to each of the test columns. Each control valve is coupled between a respective test column and the bypass tube. The control system performs operations including: controlling the control valves to fluidly couple the test columns to a water source; controlling a pump to circulate water from the water source into the test columns to immerse each test coupon in water; controlling the control valves to fluidly isolate the test columns from the water source and to fluidly isolate each test column from the other test columns; controlling a particular control valve to fluidly couple a particular test column to a biocide source; and controlling the pump to circulate biocide from the biocide source into the particular test column to immerse the test coupons in the particular test column in biocide.

21 Claims, 9 Drawing Sheets

(56) References Cited

U.S. PATENT DOCUMENTS

| | | | | |
|---|---|---|---|---|
| 2010/0059226 | A1* | 3/2010 | Termine | E21B 43/26 |
| | | | | 166/308.1 |
| 2013/0192360 | A1* | 8/2013 | Jamison | E21B 21/00 |
| | | | | 73/152.19 |
| 2013/0270006 | A1* | 10/2013 | Selman | E21B 49/005 |
| | | | | 175/24 |
| 2021/0017567 | A1* | 1/2021 | Safarian | A01N 33/12 |

OTHER PUBLICATIONS

PSBiofilm.com [online], "PS Biofilm" 2015, [retrieved on Oct. 15, 2020], retrieved from: URL <https://www.psbiofilm.com/ps-biofilm/>, 44 pages.

PCT International Search Report and Written Opinion in International Appln. No. PCT/US2021/041241, dated Dec. 23, 2021, 18 pages.

* cited by examiner

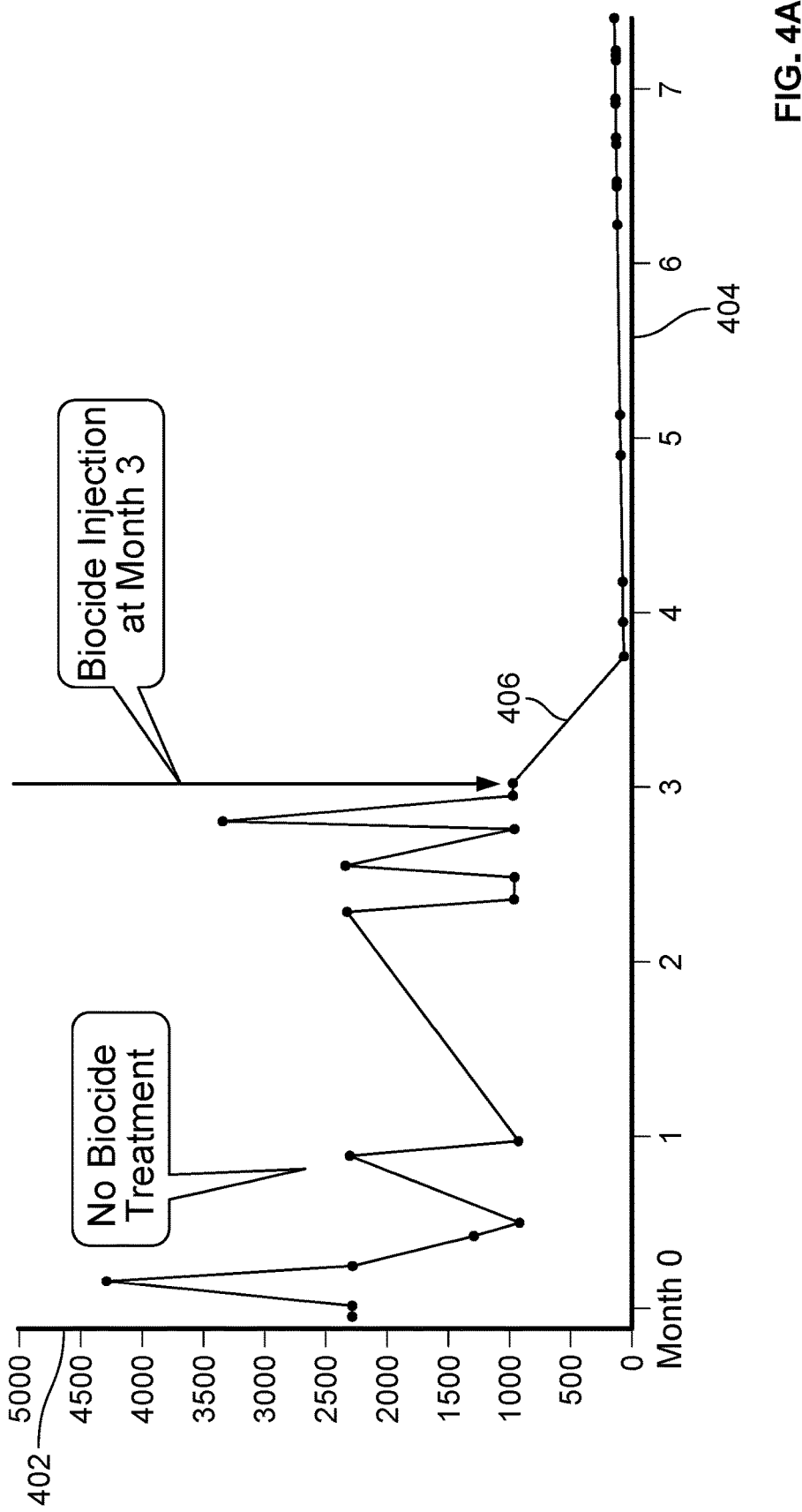

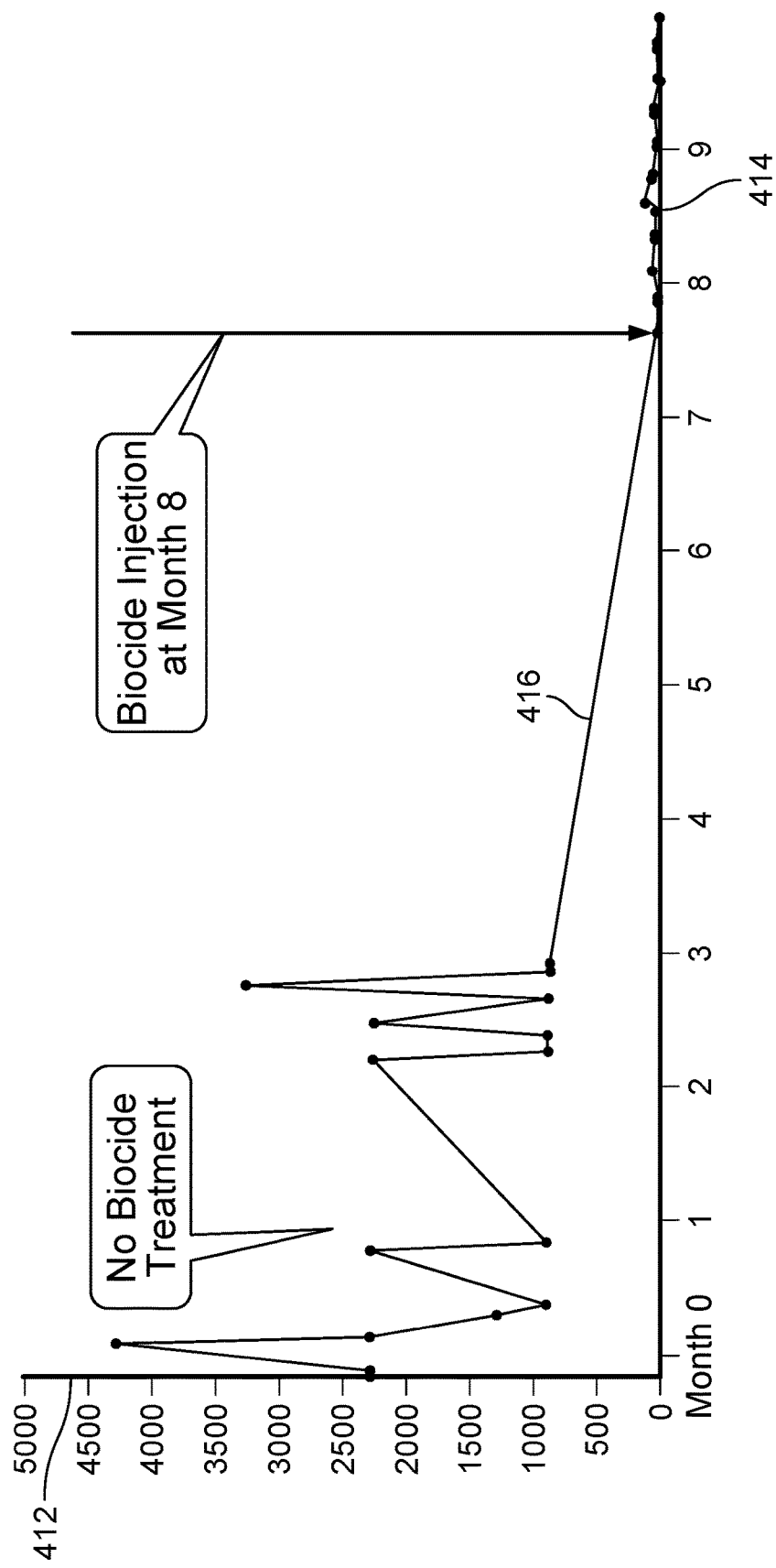

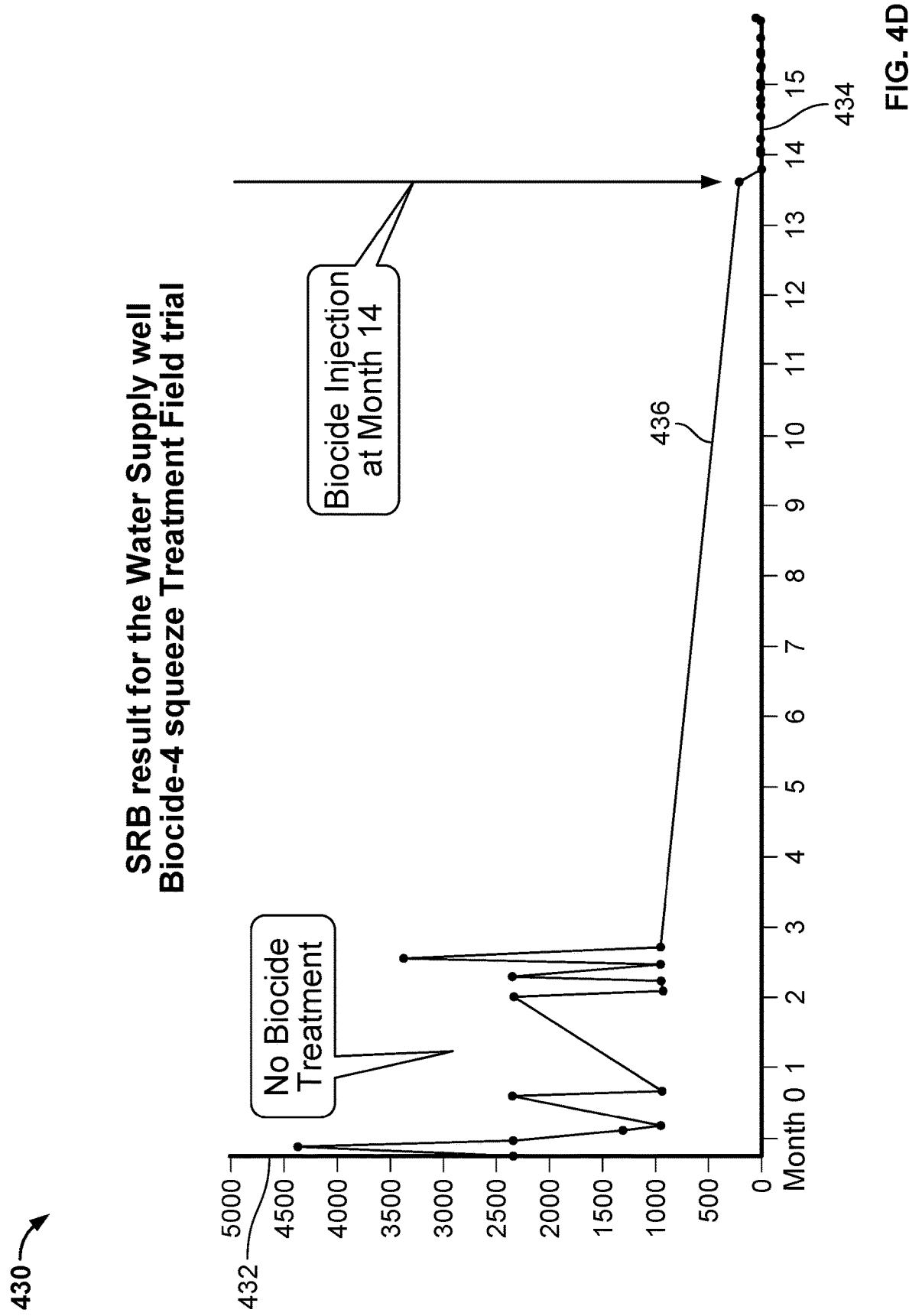

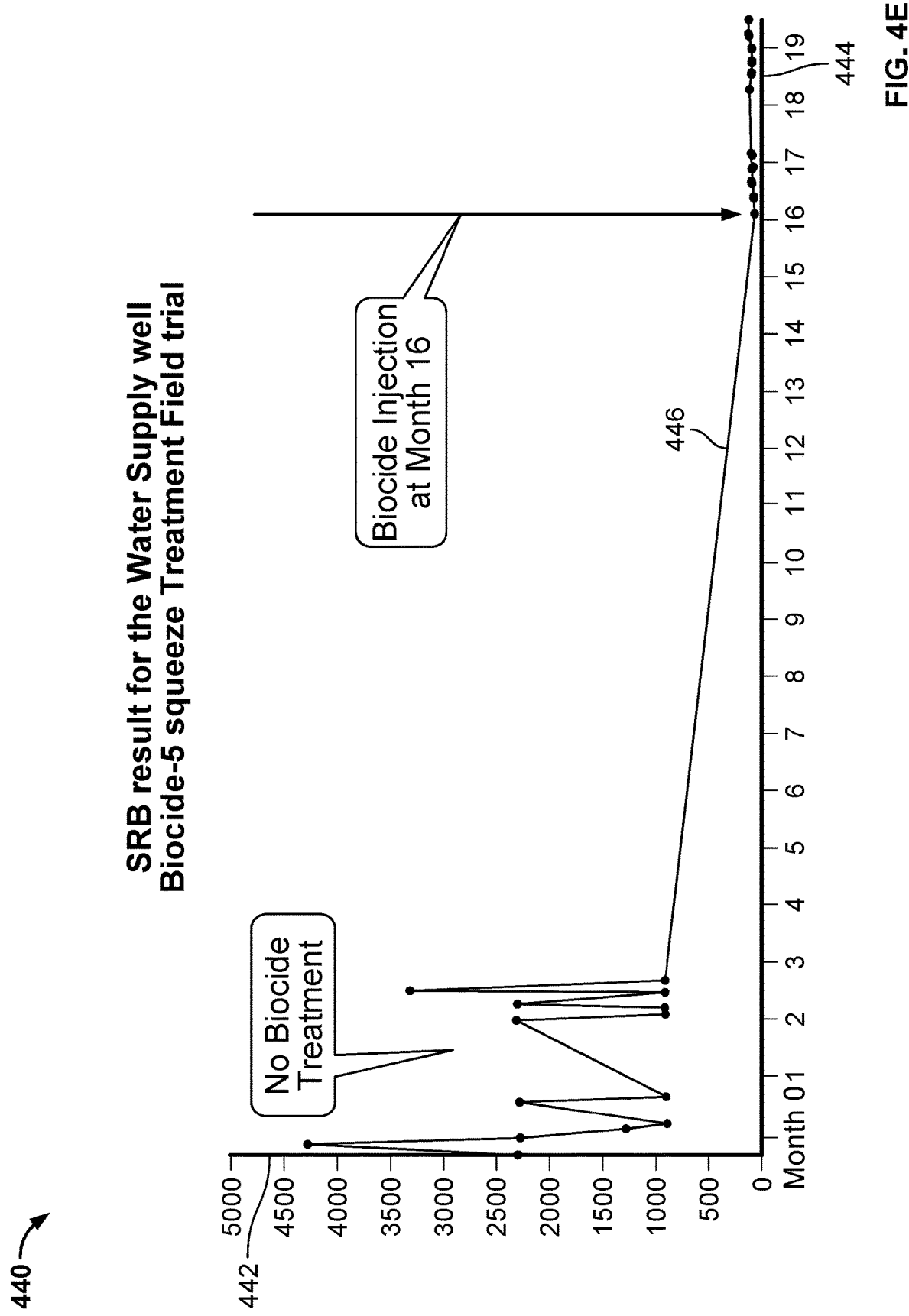

SYSTEMS AND METHODS FOR TESTING BIOCIDE

TECHNICAL FIELD

This disclosure relates to systems and methods for testing biocide and, more particularly, testing biocide used in a wellbore treatment fluid.

BACKGROUND

Water and other fluids are often used in the production of hydrocarbon fluids, such as oil or gas, from wells that are drilled into one or more subterranean formations from a terranean surface. The water and other fluids are used in, for example, a drilling process, completion processes, as well as secondary recovery processes. In some cases, planktonic and sessile bacteria, for example, may infect a supply of the water or other fluids, which can create a biomass in the water supply and affect the permeability of the subterranean formation if introduced into the well. Often, biocide or bactericide is used to kill the planktonic and sessile bacteria in the water supply.

SUMMARY

This disclosure describes implementations of a biocide testing system. In some aspects, the biocide testing system includes multiple test columns, each of which may be fluidly isolated to hold water and one or more test coupons on which biomass or bacterial growth can occur. Either simultaneously or sequentially, one or multiple different biocides may be circulated to individual test columns. Over one or more time periods, an effectiveness of each of the biocides may be determined.

In an example implementation, a biocide test rig includes a first test column; a second test column; a bypass conduit; and a loop conduit. The first test column includes a first test conduit having a first inner volume sized to receive a first plurality of test coupons, the first inner volume including a first flow path sized to receive a flow of fluid, and a first three-way control valve coupled to a bottom end of the first test conduit. The second test column includes a second test conduit having a second inner volume sized to receive a second plurality of test coupons, the second inner volume including a second flow path sized to receive the flow of fluid, and a second three-way control valve coupled to a bottom end of the second test conduit. The bypass conduit is fluidly coupled to the first and second three-way control valves. The loop conduit is fluidly coupled to a top end of the first test conduit and the second three-way control valve. Each of the first and second three-way control valves is operable to selectively fluidly couple at least two of the first test conduit, the second test conduit, the loop conduit, and the bypass conduit to circulate the flow of fluid.

In an aspect combinable with the example implementation, the loop conduit includes a first loop conduit, and the system further includes a third test column that includes: a third test conduit having a third inner volume sized to receive a third plurality of test coupons, the third inner volume including a third flow path sized to receive the flow of fluid, and a third three-way control valve coupled to a bottom end of the third test conduit.

Another aspect combinable with any of the previous aspects further includes a second loop conduit fluidly coupled to a top end of the second test conduit and the third three-way control valve.

In another aspect combinable with any of the previous aspects, the third three-way control valve is operable to selectively fluidly couple at least two of the second test conduit, the third test conduit, the second loop conduit, and the bypass conduit to circulate the flow of fluid.

Another aspect combinable with any of the previous aspects further includes a third loop conduit fluidly coupled to a top end of the third test conduit and the bypass conduit; a two-way control valve mounted in the third loop conduit; and a fluid outlet fluidly connected to the two-way control valve.

Another aspect combinable with any of the previous aspects further includes a fluid inlet at the first three-way control valve to receive the flow of fluid from a source of the fluid.

Another aspect combinable with any of the previous aspects further includes a first actuator controllably coupled to the first three-way control valve; and a second actuator controllably coupled to the second three-way control valve.

In another aspect combinable with any of the previous aspects, at least one of the first or second actuators includes a manual valve actuator.

In another aspect combinable with any of the previous aspects, the first three-way control valve, the first test conduit, the loop conduit, the second three-way control valve, and the second test conduit include a fluid flow circuit.

In another aspect combinable with any of the previous aspects, the first and second three-way control valves are operable to control the flow of the fluid through the fluid flow circuit from an inlet, to the first three-way control valve, from the first three-way control valve to the first test conduit, from the first test conduit to the loop conduit, from the loop conduit to the second three-way control valve, and from the second three-way control valve to the second test conduit.

In another aspect combinable with any of the previous aspects, the fluid includes at least one of water or biocide.

In another example implementation, a method for testing one or more biocides include controlling a first three-way control valve to fluidly couple a source of water to a first test conduit of a first test column of a biocide testing system; circulating a flow of the water into a first inner volume of the first test conduit; immersing a first plurality of test coupons positioned in the first inner volume in at least a portion of the flow of water; fluidly coupling the first test conduit with a second test conduit of a second test column of the biocide testing system by opening a second three-way control valve coupled to a first loop conduit that is coupled between the first test conduit and the second test conduit; circulating the flow of the water into a second inner volume of the second test conduit; immersing a second plurality of test coupons positioned in the second inner volume in at least another portion of the flow of water; controlling the second three-way control valve to fluidly isolate the first test column from the second test column; and after a first time duration, fluidly coupling a source of a first biocide to the first test conduit by opening the first three-way control valve, circulating a flow of the first biocide into the first inner volume of the first test conduit, immersing the first plurality of test coupons positioned in the first inner volume in at least a portion of the first biocide, and determining an effectiveness of the first biocide based on the immersion of the first plurality of test coupons in the portion of the first biocide.

An aspect combinable with the example implementation further includes, after a second time duration, fluidly coupling a source of a second biocide to the second test conduit through a bypass conduit by opening the second three-way control valve; circulating a flow of the second biocide into the second inner volume of the second test conduit; immersing the second plurality of test coupons positioned in the second inner volume in at least a portion of the second biocide; and determining an effectiveness of the second biocide based on the immersion of the second plurality of test coupons in the portion of the second biocide.

Another aspect combinable with any of the previous aspects further includes fluidly coupling the second test conduit with a third test conduit of a third test column of the biocide testing system by opening a third three-way control valve coupled to a second loop conduit that is coupled between the second test conduit and the third test conduit; circulating the flow of the water into a third inner volume of the third test conduit; immersing a third plurality of test coupons positioned in the third inner volume in at least another portion of the flow of water; and fluidly isolating the first and second test columns from the third test column by closing the third three-way control valve.

Another aspect combinable with any of the previous aspects further includes, after a third time duration, fluidly coupling a source of a third biocide to the third test conduit through the bypass conduit by opening the third three-way control valve, circulating a flow of the third biocide into the third inner volume of the third test conduit, immersing the third plurality of test coupons positioned in the third inner volume in at least a portion of the third biocide, and determining an effectiveness of the third biocide based on the immersion of the third plurality of test coupons in the portion of the third biocide.

In another aspect combinable with any of the previous aspects, each of the first, second, and third biocides includes a different biocide.

In another aspect combinable with any of the previous aspects, each start time of the first, second, and third time durations is coincident, and an end time of the third time duration is subsequent in time to an end time of the second time duration, and the end time of the second time duration is subsequent in time to an end time of the first time duration.

In another aspect combinable with any of the previous aspects, a start time of the second time duration is coincident with a start time of the first time duration, and an end time of the second time duration is subsequent in time to an end time of the first time duration.

Another aspect combinable with any of the previous aspects further includes controlling the first three-way control valve to fluidly couple the first test conduit to the bypass conduit while fluidly isolating the first test conduit from the second test conduit; controlling a two-way valve to fluidly couple the bypass conduit to an outlet of the biocide testing system; and circulating the first biocide out of the first test conduit, through the bypass conduit, and through the outlet.

In another aspect combinable with any of the previous aspects, determining the effectiveness of the first biocide based on the immersion of the first plurality of test coupons in the portion of the first biocide includes calculating a bacterial growth rate over time of bacteria formed on the first plurality of test coupons over the first time duration.

In another aspect combinable with any of the previous aspects, controlling the first three-way control valve includes commanding, with a control system communicably coupled to a first valve actuator coupled to the first three-way control valve, the first valve actuator to adjust the first three-way control valve to fluidly couple the source of water to the first test conduit.

In another example implementation, a biocide testing system includes a plurality of test columns, a bypass tube, a plurality of control valves, and a control system communicably coupled to each of the plurality of control valves. Each of the plurality of test columns includes a volume that encloses a plurality of biocide test coupons, where adjacent pairs of test columns of the plurality of test columns are fluidly coupled by respective loop conduits. The bypass tube is fluidly coupled to each of the plurality of test columns. Each control valve is coupled between a respective test column and the bypass tube. The control system is configured to perform operations including: controlling the plurality of control valves to fluidly couple the plurality of test columns to a water source; controlling at least one pump to circulate water from the water source into each of the plurality of test columns to immerse each plurality of test coupons in water; controlling the plurality of control valves to fluidly isolate the plurality of test columns from the water source and to fluidly isolate each test column from the other test columns of the plurality of test columns; controlling a particular control valve to fluidly couple a particular test column to a biocide source; and controlling the at least one pump to circulate biocide from the biocide source into the particular test column to immerse the plurality of test coupons in the particular test column in biocide.

In an aspect combinable with the example implementation, the control system is configured to perform further operations including controlling another particular control valve to fluidly couple another particular test column to another biocide source different from the biocide source; and controlling the at least one pump to circulate another biocide from the another biocide source into the another particular test column to immerse the plurality of test coupons in the another particular test column in the another biocide.

In another aspect combinable with any of the previous aspects, the control system is configured to perform further operations including determining an effectiveness of the biocide after a first time period; and determining an effectiveness of the another biocide after a second time period longer than the first time period.

In another aspect combinable with any of the previous aspects, determining the effectiveness of the biocide includes calculating a bacterial growth rate over time of bacteria formed on the plurality of test coupons in the particular test column over the first time period.

In another aspect combinable with any of the previous aspects, determining the effectiveness of the another biocide includes calculating a bacterial growth rate over time of bacteria formed on the plurality of test coupons in the another particular test column over the second time period.

In another aspect combinable with any of the previous aspects, the control system is configured to perform further operations including comparing the determined effectiveness of the biocide with the determined effectiveness of the another biocide; and determining which of the biocide or the another biocide has a greater effectiveness.

Implementations of a biocide testing system according to the present disclosure may include one or more of the following features. For example, a biocide testing system according to the present disclosure may be used online (for example, on-site) and may sequentially test multiple biocides or bactericides for their effectiveness. As another example, as an online test system, a biocide testing system according to the present disclosure may facilitate a treatment program under field conditions using samples of injected water and water supply well squeeze treatments. Also, a biocide testing system according to the present disclosure may be used to test and evaluate the performance of several biocides in sequence without having to re-build biomass on test coupons. As another example, a biocide testing system according to the present disclosure may reduce a time frame that is required to conduct several biocide chemical in-situ tests. As a further example, a biocide testing system according to the present disclosure may be a more cost efficient and economical approach for the risk assessment of bio-corrosion at a well site relative to conventional biocide test systems.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

FIGS. 4A-4E are graphs that illustrate experimental results of a biocide testing system according to the present disclosure.

DETAILED DESCRIPTION

The present disclosure describes a biocide testing system. In some aspects, the biocide testing system includes multiple test columns, each of which may be fluidly isolated to hold water and one or more test coupons on which biomass or bacterial growth can occur. Either simultaneously or sequentially, one or multiple different biocides may be circulated to individual test columns. Over one or more time periods, an effectiveness of each of the biocides may be determined.

Figure 1:
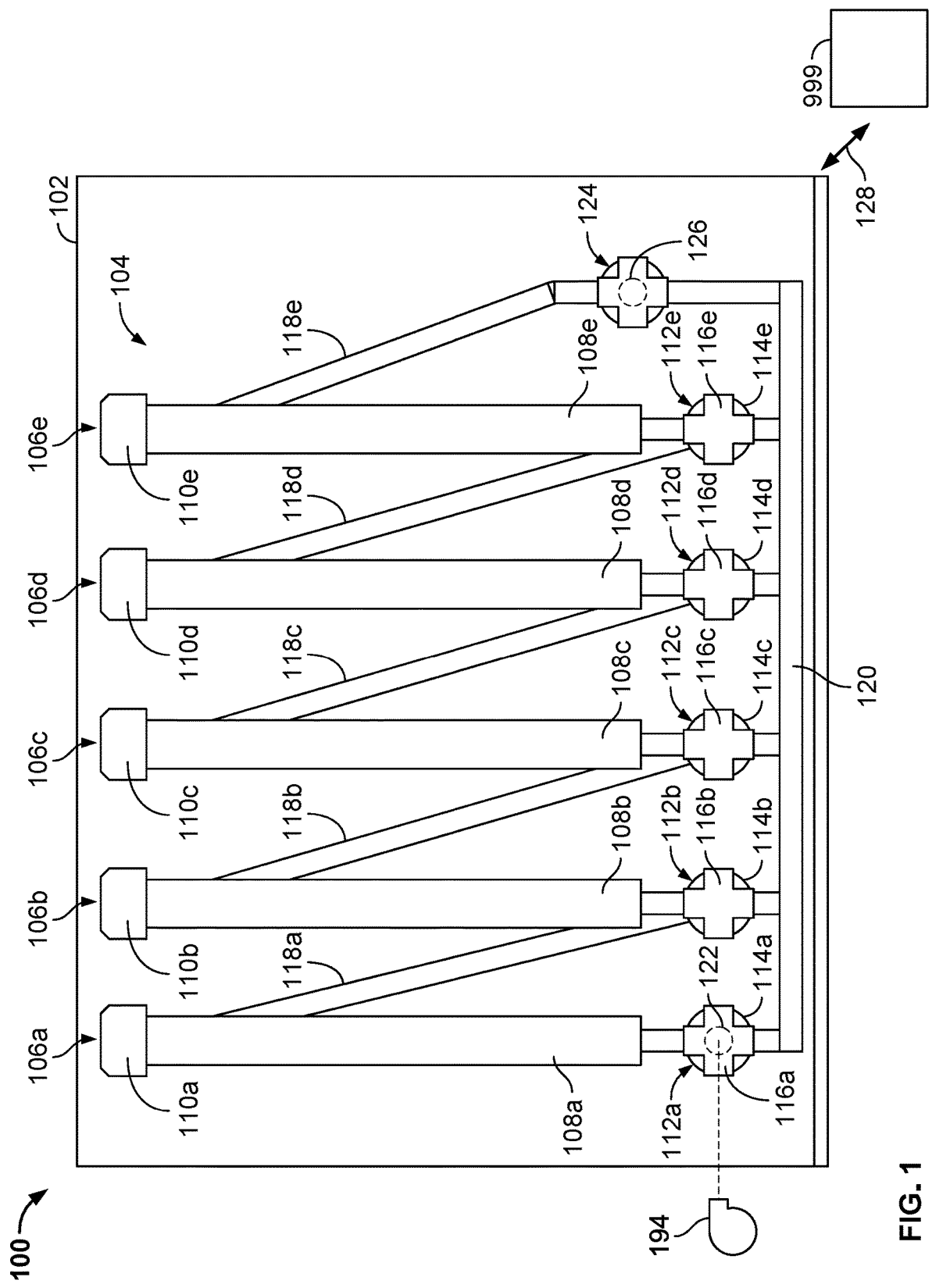
FIG. 1 is a schematic diagram of a front view of an example implementation of a biocide testing system according to the present disclosure.

FIG. 1 is a schematic diagram of a front view of an example implementation of a biocide testing system 100 according to the present disclosure. Generally, the biocide testing system 100 can be operated (for example, manually by a human operator or automatically by a control system) to test and evaluate a performance of several biocides in sequence (for example, five biocides in this example implementation) at the same time, which may reduce a time frame that is required to conduct several biocides chemical evaluation in situ relative to conventional biocide test systems. In some aspects, biocides or bactericides are used in water-based drilling fluids that are vulnerable to bacterial attack. Bactericides or biocides (as those terms are used interchangeably in the present disclosure) can be used to control sulfate-reducing bacteria, slime-forming bacteria, iron-oxidizing bacteria, and bacteria that attacks polymers in fracture and secondary recovery fluids. Without such biocides, the formation of a large biomass in the water or drilling fluid could occur, which could plug a subterranean formation and reduce a permeability of the formation.

As shown in FIG. 1, the biocide testing system 100 includes a biocide testing rig 104 that is mounted or attached to a stand (or support) 102. The biocide testing rig 104 includes multiple test columns 106a-106e. In this example, there are five test columns 106a-106e; alternative implementations of the biocide testing system 100 may include more or fewer test columns 106a-106e. Generally, each test conduit 108a-108e may be fluidly isolated from one or more (including all) of the other test conduits 108a-108e, as well as other components of the biocide testing rig 104. As shown in this example, each test column 106a-106e is fluidly coupled to a bypass conduit 120 that extends from (and is fluidly coupled to) test column 106a to test column 106e. As used in the present disclosure, a "fluid" is a liquid, a gas, or a mixed-phase fluid (in other words, part liquid and part gas).

In this example implementation, each test column 106a-106e includes a respective cap 110a-110e that fluidly encloses a respective test conduit 108a-108e at one end (for example, a top end) of the respective test conduit 108a-108e. Each test column 106a-106e further includes a respective control valve assembly 112a-112e fluidly coupled between another end (for example, a bottom end) of the respective test conduit 108a-108e and the bypass conduit 120. Each control valve assembly 112a-112e, in this example implementation, includes a control valve 114a-114e, such as a three-way control valve 114a-114e and a respective valve actuator 116a-116e. In some aspects, one or more of the valve actuators 116a-116e is a manual valve actuator and is operable to adjust the respective control valve 114a-114e through human (or human-operated machine) control. In alternative aspects, one or more of the valve actuators 116a-116e is an automated valve actuator and is operable to control the respective control valve 114a-114e through signals (or commands) 128 received from, for example, a control system 999.

In some implementations, the control system 999 is a microprocessor-based control system that includes one or more hardware processors, one or more memory modules communicably coupled to the hardware processor(s), and instructions and data encoded on the one or more memory modules. The hardware processor(s) are operable to execute the instructions to perform operations, including operations described in the present disclosure. As shown in this example (for example, by the bi-directional signals 128), the control system 999 may be communicably coupled (wired or wirelessly) to, for instance, the respective actuators 116a-116e of the control valve assemblies 112a-112e, the valve 124, and one or more sensors positioned in or on one or more components of the biocide testing rig 104 (for example, within the test conduits 108a-108e). The control system 999 may also be communicably coupled to one or more pumps 194 that are used to circulate one or more fluids (such as water 190 or biocide 192) through the biocide testing system 100 (for example, through the inlet 122 as shown in FIG. 1).

In some aspects, the signals 128 may represent commands from the control system 999 to one or more of the respective actuators 116a-116e of the control valve assemblies 112a-112e, the valve 124, or one or more sensors positioned in or on one or more components of the biocide testing rig 104. In some aspects, the signals 128 may represent feedback (for example, valve opening percentage) or measurements (for example, temperature, pressure, or other measured parameter) from the one or more of the respective actuators 116a-116e of the control valve assemblies 112a-112e, the valve 124, or one or more sensors positioned in or on one or more components of the biocide testing rig 104 to the control system 999.

As shown in this example, a fluid inlet 122 is positioned at or part of the control valve 114a. In some aspects, one or more fluids (such as water and one or more biocide fluids) may be introduced into the biocide testing rig 104 through the fluid inlet 122. Once introduced into the biocide testing rig 104, the one or more fluids may exit the biocide testing rig 104 at a fluid outlet 126.

As further shown in this example, loop conduits 118a-118e are fluidly coupled within the biocide testing rig 104. In this example having five test columns 106a-106e, each of the loop conduits 118a-118e is fluidly coupled between a particular test conduit 108a-108d and a particular control valve 114b-114e. As further shown in this example, each control valve 114a-114e is fluidly coupled at three locations. The control valve 114a is fluidly coupled to (or includes) the fluid inlet 122, the test conduit 108a (at a bottom end), and the bypass conduit 120. The control valve 114b is fluidly coupled to the loop conduit 118a (which is also fluidly coupled to a top end of the test conduit 108a), the test conduit 108b (at a bottom end), and the bypass conduit 120. The control valve 114c is fluidly coupled to the loop conduit 118b (which is also fluidly coupled to a top end of the test conduit 108b), the test conduit 108c (at a bottom end), and the bypass conduit 120. The control valve 114d is fluidly coupled to the loop conduit 118c (which is also fluidly coupled to a top end of the test conduit 108c), the test conduit 108d (at a bottom end), and the bypass conduit 120. The control valve 114e is fluidly coupled to the loop conduit 118d (which is also fluidly coupled to a top end of the test conduit 108d), the test conduit 108e (at a bottom end), and the bypass conduit 120.

In this example, the loop conduit 118e is fluidly coupled to a top end of the test conduit 108e and the bypass conduit 120 and includes the fluid outlet 126 at the valve 124. In some aspects, the valve 124 (which also includes a manual or automated actuator) is a two-way valve, such as a shut-off valve. Thus, in a closed position, the valve 124 may restrict or prevent fluid from flowing from the biocide testing rig 104 through the outlet 126.

Figure 2A:
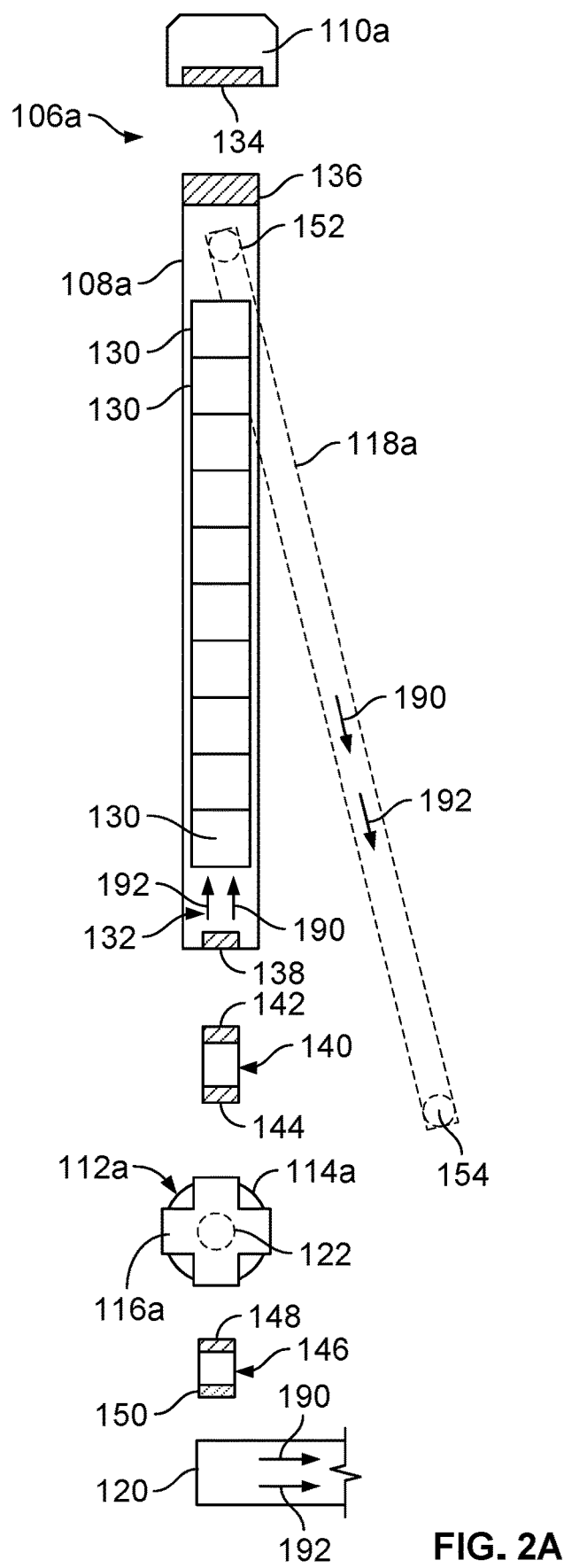
FIGS. 2A-2B are schematic diagrams of a front exploded view and a side exploded view of portions of the example implementation of the biocide testing system of FIG. 1
Figure 2B:
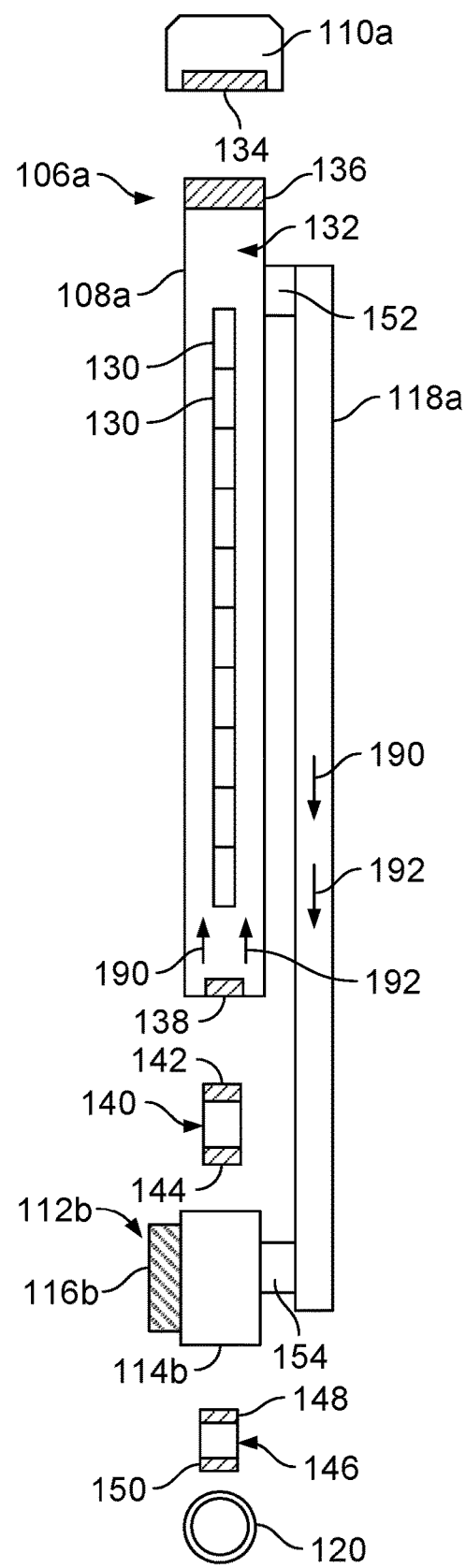

Turning to FIGS. 2A-2B, these figures are schematic diagrams of a front exploded view and a side exploded view of portions of the example implementation of the biocide testing system 100 of FIG. 1. FIG. 2A shows a front exploded view of the test column 106a. Test columns 106b-106e, in this example implementation of the biocide testing system 100, include or have a similar structure as the test column 106a. As shown, the cap 110a includes a connection 134 (for example, threaded) that connects to a connection 136 (for example, threaded) at the top end of the test conduit 108a. An inlet 152 of loop conduit 118a is connected at or near the top end of the test conduit 108a. The test conduit 108a includes a volume 132 into which multiple test coupons 130 may be inserted or positioned. Each test coupon 130 may be formed from steel, other metal, or a non-metallic material supportive of biomass growth thereon.

In this example implementation, a bottom end of the test conduit 108a includes a connection 138 (for example, threaded) that may couple to a connection 142 (for example, threaded) of a coupling 140. In turn another connection 144 (for example, threaded) of the coupling 140 may connect (both physically and fluidly) to the control valve assembly 112a. The control valve assembly 112a may also connect to another coupling 146 through a connection 148 (for example, threaded). The coupling 146 may then connect with a connection 150 (for example, threaded) to the bypass conduit 120.

Turning briefly to FIG. 2B, this figure shows a side exploded view of the test column 106a. As shown in this figure, the loop conduit 118a, which is fluidly coupled to the test conduit 108a at inlet 152, includes an outlet that is fluidly coupled to the control valve assembly 112b (and more specifically, the control valve 114b as shown). The control valve assembly 112b also connects to another coupling 146 through a connection 148 (for example, threaded). The coupling 146 may then connect with a connection 150 (for example, threaded) to the bypass conduit 120 to fluidly connect the control valve 114b to the bypass conduit 120.

As shown in FIGS. 2A-2b, and more fully explained later, one or more fluids 190 and 192 may be circulated through the biocide testing rig 104 to test and evaluate one or more biocides (for example, Biotreat 1451, SM-BM-7055, ROIM-B255, or BIOC-16039) in removing biomass built up on one or more of the test coupons 130. For example, water 190 may be circulated through each test column 106a-106e to contact the test coupons 130 positioned in each test conduit 108a-108e. Subsequent to the generation of biomass on one or more of the test coupons 130 in each of the test conduits 108a-108e, a particular biocide 192 may be circulated to each respective test conduit 108a-108e to treat the biomass generated on the test coupons 130 in that respective test conduit 108a-108e. The particular biocide 192 may mix with the water 190 in each respective test conduit 108a-108e or may, in some aspects, replace the water 190 within each respective test conduit 108a-108e (which subsequently flows out of the biocide testing rig 104 through the outlet 126).

The circulation of water 190 and each particular biocide 192 may be sequentially performed through manipulation of the control valve assemblies 112a-112e to selectively connect two out of three of the particular conduits of the biocide testing rig 104 that are connected to each particular control valve assembly 112a-112e, while fluidly isolating a third of the three particular conduits from the two fluidly coupled conduits. For example, control valve 114a may be manipulated (manually or automatically) to: 1) fluidly connect the inlet 122 to the test conduit 108a; 2) fluidly connect the inlet 122 to the bypass conduit 120; or 3) fluidly connect the test conduit 108a to the bypass conduit 120. Control valve 114b may be manipulated (manually or automatically) to: 1) fluidly connect test conduit 108b to test conduit 108a through loop conduit 118a; 2) fluidly connect the test conduit 108a to the bypass conduit 120 through the loop conduit 118a; or 3) fluidly connect the test conduit 108b to the bypass conduit 120. Control valve 114c may be manipulated (manually or automatically) to: 1) fluidly connect test conduit 108c to test conduit 108b through loop conduit 118b; 2) fluidly connect the test conduit 108b to the bypass conduit 120 through the loop conduit 118b; or 3) fluidly connect the test conduit 108c to the bypass conduit 120. Control valve 114d may be manipulated (manually or automatically) to: 1) fluidly connect test conduit 108d to test conduit 108c through loop conduit 118c; 2) fluidly connect the test conduit 108c to the bypass conduit 120 through the loop conduit 118c; or 3) fluidly connect the test conduit 108d to the bypass conduit 120. Control valve 114e may be manipulated (manually or automatically) to: 1) fluidly connect test conduit 108e to test conduit 108d through loop conduit 118d; 2) fluidly connect the test conduit 108d to the bypass conduit 120 through the loop conduit 118d; or 3) fluidly connect the test conduit 108e to the bypass conduit 120.

Figure 3:
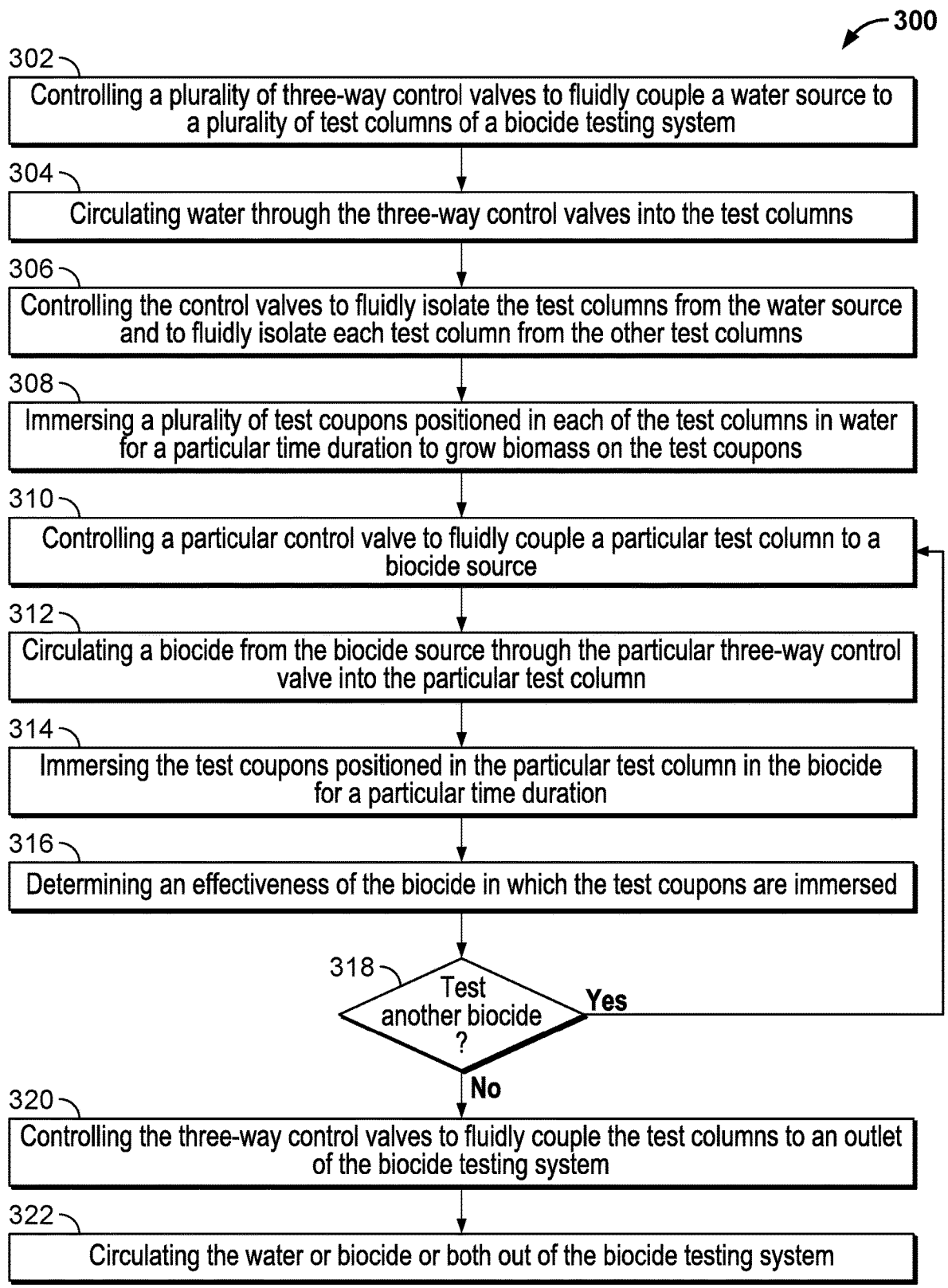
FIG. 3 illustrates a flowchart that describes an example method of operating a biocide testing system according to the present disclosure.

FIG. 3 illustrates a flowchart that describes an example method 300 of operating the biocide testing system 100 of FIGS. 1 and 2A-2B. Method 300 may begin at step 302, which includes controlling a plurality of three-way control valves to fluidly couple a water source to a plurality of test columns of a biocide testing system. For example, with reference to biocide testing system 100, in some aspects, all of the control valves 114a-114e may be controlled to fluidly couple the test columns 106a-106e with the inlet 122 through which water may be circulated. In some aspects, the control valves 114a-114e may be controlled to fluidly couple each test column 106a-106e with the bypass conduit 120. In other aspects, the control valves 114a-114e may be controlled to fluidly couple each test column 106b-106e with the test column 106a through the loop conduits 108a-108d. Prior to step 302, test coupons 130 may be positioned within each test conduit 108a-108e.

Method 300 may continue at step 304, which includes circulating water through the three-way control valves into the test columns. For example, water may be circulated from a source of water to each of the test column 106a-106e once they are fluidly coupled to the inlet 122. The water may be fresh water or brine. In some aspects, the water may include bacteria or other material that encourages biomass growth on the test coupons 130.

Method 300 may continue at step 306, which includes controlling the control valves to fluidly isolate the test columns from the water source and to fluidly isolate each test column from the other test columns. For example, once water has filled each of the test conduits 108a-108e, the control valves 114a-114e may be controlled to close any additional fluid communication from the inlet 122 to the test conduits 108a-108e, to close any fluid communication between the test conduits 108a-108e, and to close fluid communication from the test conduits 108a-108e to the outlet 126. In some aspects, valve 124 is also controlled in step 306 to close fluid communication from the test conduits 108a-108e to the outlet 126. Thus, subsequent to step 306, each of the test columns 106a-106e may be filled with water and sealed against loss of water to other parts of the biocide testing rig 104 or external to the biocide testing rig 104.

Method 300 may continue at step 308, which includes immersing a plurality of test coupons positioned in each of the test columns in water for a particular time duration to grow biomass on the test coupons. For example, once sealed, each test column 106a-106e may be filled with water, which immerses the test coupons 130 in each test conduit 108a-108e, thereby promoting biomass growth on the test coupons 130. Step 308 may continue for a time duration sufficient to grow enough biomass on the test coupons 130 to adequately test an effectiveness of one or more biocides in eliminating such biomass. In some aspects, the particular time duration may be days, weeks, months, or other time duration.

Method 300 may continue at step 310, which includes controlling a particular control valve to fluidly couple a particular test column to a biocide source. For example, as a first test iteration of steps 310-316, test column 106a may be selected to test a particular biocide (for instance, a first biocide) from a number of possible biocides. Control valve 114a is controlled (for example, manually or by control system 999 through actuator 116a) to fluidly couple the test conduit 108a to the biocide source. Control valves 114b-114e, in step 310, remain closed in that they prevent fluid communication between test conduits 108b-108e and test conduit 108a (as well as the inlet 122 and outlet 126). As noted previously, example biocides include Biotreat 1451, SM-BM-7055, ROIM-B255, or BIOC-16039, among others.

Method 300 may continue at step 312, which includes circulating a biocide from the biocide source through the particular three-way control valve into the particular test column. For example, once control valve 114a is controlled to fluidly couple test conduit 108a with the biocide source, the selected biocide may be circulated (for example, by one or more pumps 194) into the test conduit 108a through the inlet 122. In some aspects, step 312 may also include controlling the control valve 114a to first establish fluid communication between the test conduit 108a and the bypass conduit 120 in order to drain water out of the test conduit 108a (for example, through the outlet 126) prior to circulating the selected biocide into the test conduit 108a. Further, in some aspects, step 312 may include controlling the control valve 114a to fluidly isolate the test conduit 108a from the other test conduits 108b-108e and the bypass conduit 120 once the selected biocide is circulated into the test conduit 108a.

Method 300 may continue at step 314, which includes immersing the test coupons positioned in the particular test column in the biocide for a particular time duration. For example, once the selected biocide is circulated into test conduit 108a, the test coupons 130 with biomass growth are allowed to immerse in the biocide for a particular time period, be that days, weeks, months, or otherwise.

Method 300 may continue at step 316, which includes determining an effectiveness of the biocide in which the test coupons are immersed. For example, in some aspects, after the expiration of the particular time period or duration (or several times during the particular time period) of step 314, the test coupons 130 in test conduit 108a may be removed (for example, by opening cap 110a) and examined for biomass growth. In some aspects, a determination is made as to an amount of bacterial growth rate on the test coupons 130 relative to an amount of time in which the test coupons 130 have been immersed in the particular biocide. An effectiveness of the biocide may be determined based on, for example, a reduction of bacterial growth over time. Thus, as noted, step 316 may occur more than once during the particular time period of step 314, as well as at the end of the time period of 114.

Method 300 may continue at step 318, which includes a decision of whether or not to test another biocide. For example, as shown, the biocide testing system 100 includes five test columns 106a-106e; therefore, five different biocides can be tested simultaneously or sequentially. In the case of simultaneous testing, for example, after step 308, the sequence of steps 310-316 may be repeated five times. In each repetition of the sequence of steps 310-316, a different test column 106a-106e may be selected and tested with a different biocide. For example, if the decision at step 318 is "yes," then method 300 may return to step 310. Upon the second iteration of step 310, test column 106b may be selected to test another particular biocide (for instance, a second biocide) from a number of possible biocides. Control valve 114b is controlled (for example, manually or by control system 999 through actuator 116b) to fluidly couple the test conduit 108b to the second biocide source. Control valves 114a and 114c-114e, in the second iteration of step 310, remain closed in that they prevent fluid communication between test conduits 108a and 108c-108e and test conduit 108b (as well as the inlet 122 and outlet 126).

Method 300 may continue at a second iteration of step 312, which includes circulating a second biocide from a second biocide source through the control valve 114b into the test column 106b. For example, once control valve 114b is controlled to fluidly couple test conduit 108b with the second biocide source, the selected biocide may be circulated (for example, by one or more pumps 194) into the test conduit 108b through the inlet 122. In some aspects, step 312 may also include controlling the control valve 114b to first establish fluid communication between the test conduit 108b and the bypass conduit 120 in order to drain water out of the test conduit 108b (for example, through the outlet 126) prior to circulating the second biocide into the test conduit 108b. Further, in some aspects, the second iteration of step 312 may include controlling the control valve 114b to fluidly isolate the test conduit 108b from the other test conduits 108a and 108c-108e and the bypass conduit 120 once the second biocide is circulated into the test conduit 108a.

Method 300 may continue at a second iteration of step 314, which includes immersing the test coupons 130 positioned in the test column 106b in the second biocide for a particular time duration. For example, once the second biocide is circulated into test conduit 108b, the test coupons 130 with biomass growth are allowed to immerse in the second biocide for a particular time period, be that days, weeks, months, or otherwise.

Method 300 may continue at a second iteration of step 316, which includes determining an effectiveness of the second biocide in which the test coupons 130 are immersed. For example, in some aspects, after the expiration of the particular time period or duration (or several times during the particular time period) of the second iteration of step 314, the test coupons 130 in test conduit 108b may be removed (for example, by opening cap 110b) and examined for biomass growth. In some aspects, a determination is made as to an amount of bacterial growth rate on the test coupons 130 relative to an amount of time in which the test coupons 130 have been immersed in the particular biocide. An effectiveness of the second biocide may be determined based on, for example, a reduction of bacterial growth over time. Thus, as noted, the second iteration of step 316 may occur more than once during the particular time period of step 314, as well as at the end of the time period of 114.

After the second iteration of steps 310-316, method 300 returns to step 318, which includes another decision of whether or not to test another biocide. As noted, in this example, biocide testing system 100 includes five test columns 106a-106e, so steps 310-316 could be repeated three additional iterations. In some aspects, each iteration of the sequence of steps 310-316 may overlap with other iterations of steps 310-316. Thus, in some aspects, steps in the sequence 310-316 in a second iteration may occur prior to the completion of one or more of the steps 310-316 in a first iteration; likewise, steps in the sequence 310-316 in a third iteration may occur prior to the completion of one or more of the steps 310-316 in a second (or first) iteration, and so on.

If the decision at step 318 is "no," then method 300 may continue at step 320, which includes controlling the three-way control valves to fluidly couple the test columns to an outlet of the biocide testing system. For example, once one or more biocides have been tested for effectiveness, the control valves 114a-114e may be controlled to fluidly couple the test conduits 108a-108e to the bypass conduit 120. Valve 124 may also be controlled to fluidly couple the bypass conduit 120 (or the loop conduit 118e, or both) to the outlet 126.

Method 300 may continue at step 320, which includes circulating the water or biocide or both out of the biocide testing system. For example, any remaining fluid, such as water, biocide(s) or a mix thereof, may be circulated out of the biocide testing rig 104 through the outlet 126.

FIGS. 4A-4E are graphs that illustrate experimental results of a biocide testing system according to the present disclosure. For example, as described with reference to method 300, step 316 includes determining an effectiveness of the biocide in which the test coupons are immersed. This determination may include a calculation (by a human operator or the control system 999) as to an amount of bacterial growth rate on the test coupons relative to an amount of time in which the test coupons have been immersed in a particular biocide. An experimental process was conducted with a biocide testing system in accordance with the present disclosure, and the graphs of FIGS. 4A-4E represent the results of such process, where five different biocides were tested for their respective effectiveness. Water from a water supply well was used in testing sulfate reducing bacteria (SRB) biocides. In each graph, points on the respective curves represent test data (for example, according to step 316). Month 0, in the illustrated graphs, represents a time in which the test coupons in each test column were immersed in water to promote bacterial growth.

FIG. 4A illustrates graph 400, which shows a curve 406 that represents bacterial growth in cells per milliliter (cells/mL) on y-axis 402 versus time in months on x-axis 404. As shown in graph 400, a first biocide was introduced into a first of the test columns at month 3. As the curve 406 shows, bacterial growth was at 500 cells/mL at month 3 and by month 4 (estimated), the bacterial growth had been reduced to about 0 cells/mL by the tested biocide.

FIG. 4B illustrates graph 410, which shows a curve 416 that represents bacterial growth in cells per milliliter (cells/mL) on y-axis 412 versus time in months on x-axis 414. As shown in graph 410, a second biocide was introduced into a second of the test columns at month 8. As the curve 416 shows, bacterial growth was already low at month 8 and remained at about 0 cells/mL by the tested biocide from month 8 through month 9.

Figure 4C:
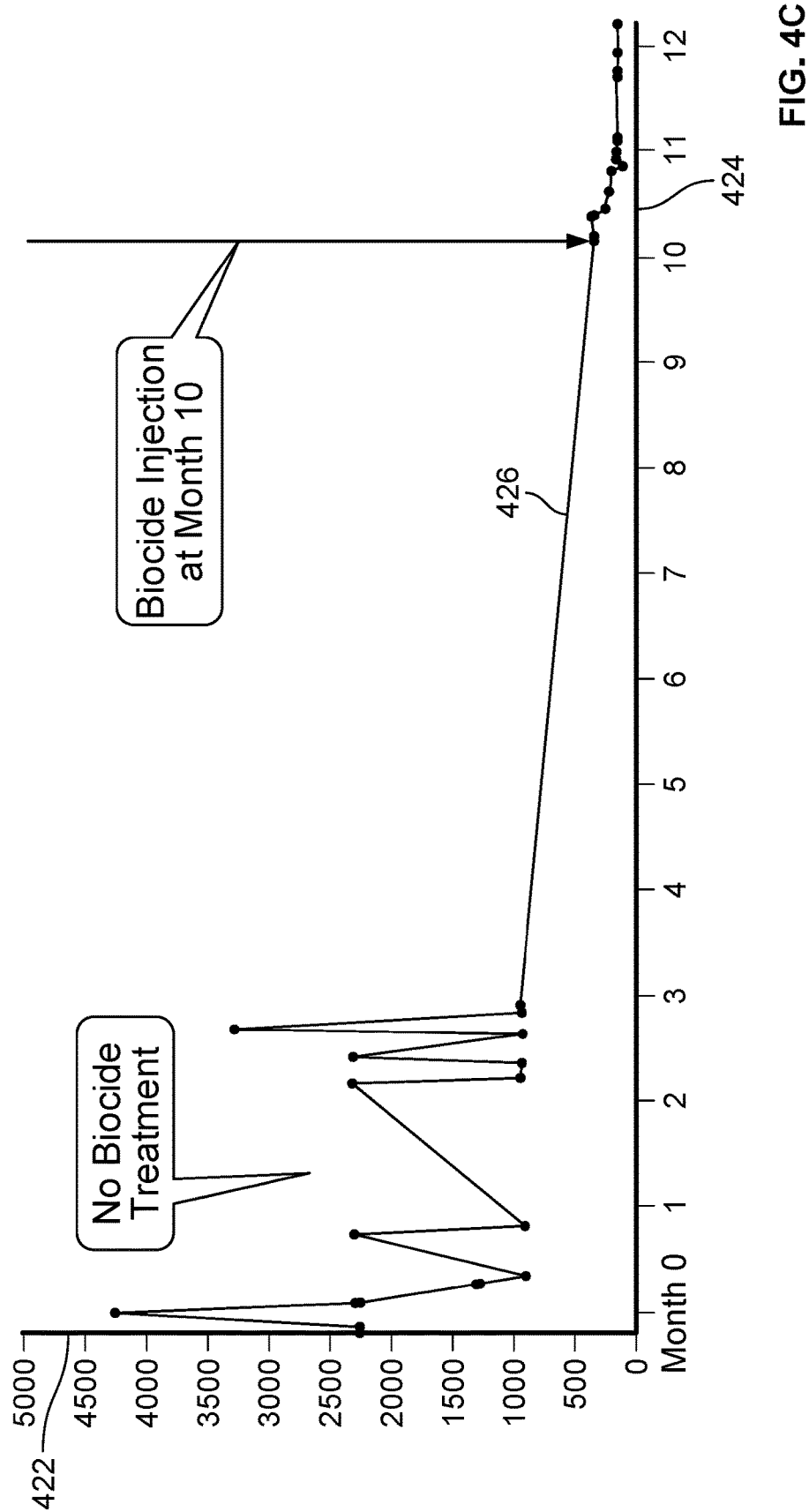

FIG. 4C illustrates graph 420, which shows a curve 426 that represents bacterial growth in cells per milliliter (cells/mL) on y-axis 422 versus time in months on x-axis 424. As shown in graph 420, a third biocide was introduced into a third of the test columns at month 10. As the curve 426 shows, bacterial growth was at about 250 cells/mL at month 10 and by month 11 (estimated), the bacterial growth had been reduced to about 0 cells/mL by the tested biocide.

FIG. 4D illustrates graph 430, which shows a curve 436 that represents bacterial growth in cells per milliliter (cells/mL) on y-axis 432 versus time in months on x-axis 434. As shown in graph 430, a fourth biocide was introduced into one of the test columns at month 14. As the curve 436 shows, bacterial growth was at about 250 cells/mL at month 14 and by month 15 (estimated), the bacterial growth had been reduced to about 0 cells/mL by the tested biocide.

FIG. 4A illustrates graph 440, which shows a curve 446 that represents bacterial growth in cells per milliliter (cells/mL) on y-axis 442 versus time in months on x-axis 444. As shown in graph 440, a fifth biocide was introduced into a fifth of the test columns at month 16. As the curve 446 shows, bacterial growth was already low at month 16 and remained at about 0 cells/mL by the tested biocide from month 16 through month 19.

Figure 5:
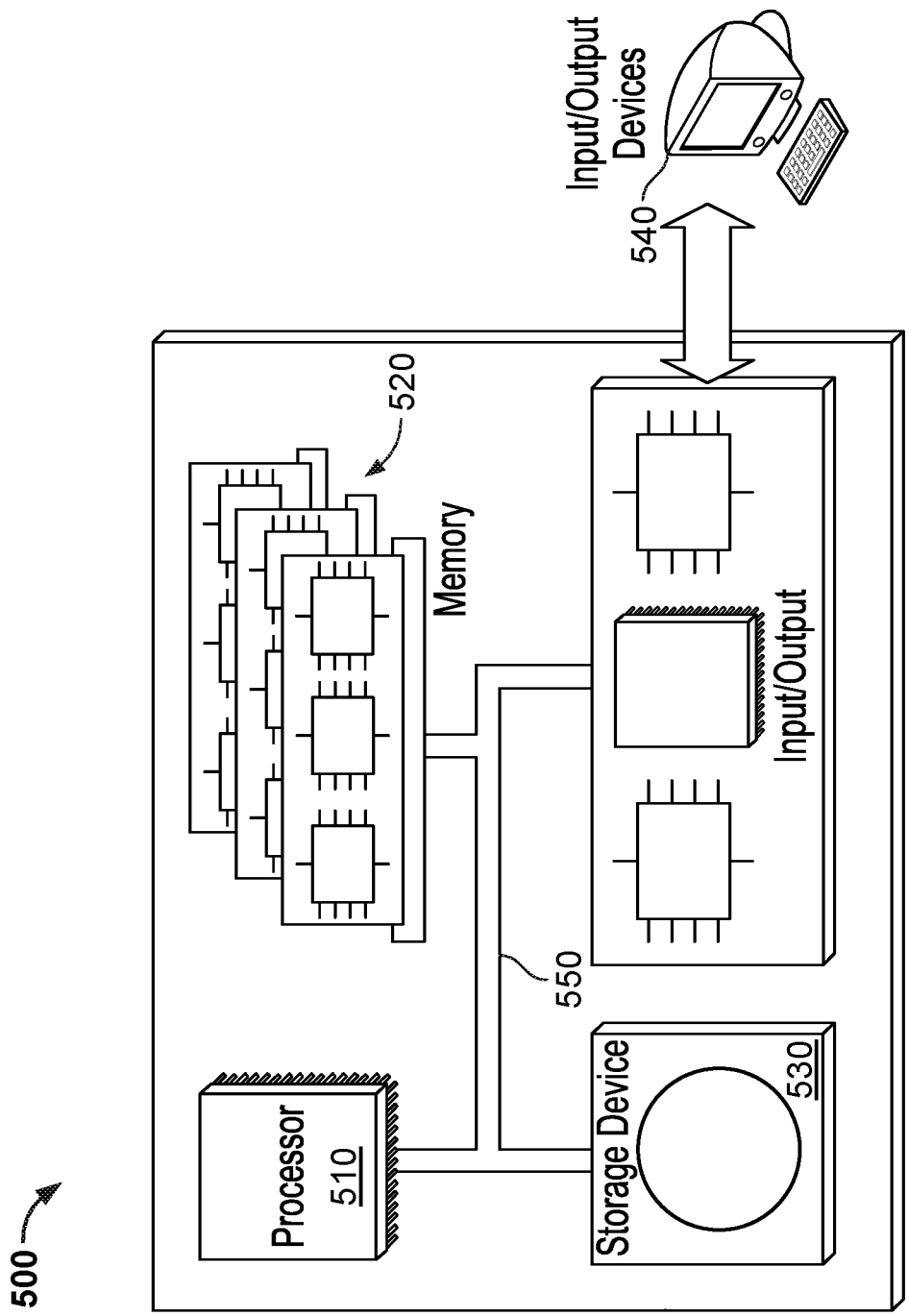
FIG. 5 is a schematic illustration of an example controller (or control system) for controlling operations of a biocide testing system according to the present disclosure.

FIG. 5 is a schematic illustration of an example controller 500 (or control system) for controlling operations of a biocide testing system according to the present disclosure. For example, the controller 500 may include or be part of the control system 999 shown in FIGS. 1 and 2A-2B. The controller 500 is intended to include various forms of digital computers, such as printed circuit boards (PCB), processors, digital circuitry, or otherwise parts of a biocide testing system. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 500 includes a processor 510, a memory 520, a storage device 530, and an input/output device 540. Each of the components 510, 520, 530, and 540 are interconnected using a system bus 550. The processor 510 is capable of processing instructions for execution within the controller 500. The processor may be designed using any of a number of architectures. For example, the processor 510 may be a CISC (Complex Instruction Set Computers) processor, a RISC (Reduced Instruction Set Computer) processor, or a MISC (Minimal Instruction Set Computer) processor.

In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the controller 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the controller 500. In one implementation, the storage device 530 is a computer-readable medium. In various different implementations, the storage device 530 may be a floppy disk device, a hard disk device, an optical disk device, or a tape device.

The input/output device 540 provides input/output operations for the controller 500. In one implementation, the input/output device 540 includes a keyboard and/or pointing device. In another implementation, the input/output device 540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A method for testing one or more biocides, comprising:
   controlling a first three-way control valve to fluidly couple a source of water to a first test conduit of a first test column of a biocide testing system;
   circulating a flow of the water into a first inner volume of the first test conduit;
   immersing a first plurality of test coupons positioned in the first inner volume in at least a portion of the flow of water;
   fluidly coupling the first test conduit with a second test conduit of a second test column of the biocide testing system by opening a second three-way control valve coupled to a first loop conduit that is coupled between the first test conduit and the second test conduit;
   circulating the flow of the water into a second inner volume of the second test conduit;
   immersing a second plurality of test coupons positioned in the second inner volume in at least another portion of the flow of water;
   controlling the second three-way control valve to fluidly isolate the first test column from the second test column; and
   after a first time duration:
      fluidly coupling a source of a first biocide to the first test conduit by opening the first three-way control valve,
      circulating a flow of the first biocide into the first inner volume of the first test conduit,
      immersing the first plurality of test coupons positioned in the first inner volume in at least a portion of the first biocide, and
      determining an effectiveness of the first biocide based on the immersion of the first plurality of test coupons in the portion of the first biocide.

2. The method of claim 1, further comprising, after a second time duration:
   fluidly coupling a source of a second biocide to the second test conduit through a bypass conduit by opening the second three-way control valve;
   circulating a flow of the second biocide into the second inner volume of the second test conduit;
   immersing the second plurality of test coupons positioned in the second inner volume in at least a portion of the second biocide; and
   determining an effectiveness of the second biocide based on the immersion of the second plurality of test coupons in the portion of the second biocide.

3. The method of claim 2, further comprising:
   fluidly coupling the second test conduit with a third test conduit of a third test column of the biocide testing system by opening a third three-way control valve coupled to a second loop conduit that is coupled between the second test conduit and the third test conduit;
   circulating the flow of the water into a third inner volume of the third test conduit;
   immersing a third plurality of test coupons positioned in the third inner volume in at least another portion of the flow of water;
   fluidly isolating the first and second test columns from the third test column by closing the third three-way control valve; and
   after a third time duration:
      fluidly coupling a source of a third biocide to the third test conduit through the bypass conduit by opening the third three-way control valve,
      circulating a flow of the third biocide into the third inner volume of the third test conduit,
      immersing the third plurality of test coupons positioned in the third inner volume in at least a portion of the third biocide, and
      determining an effectiveness of the third biocide based on the immersion of the third plurality of test coupons in the portion of the third biocide.

4. The method of claim 3, wherein each of the first, second, and third biocides comprises a different biocide.

5. The method of claim 3, wherein each start time of the first, second, and third time durations is coincident, and an end time of the third time duration is subsequent in time to an end time of the second time duration, and the end time of the second time duration is subsequent in time to an end time of the first time duration.

6. The method of claim 2, wherein a start time of the second time duration is coincident with a start time of the first time duration, and an end time of the second time duration is subsequent in time to an end time of the first time duration.

7. The method of claim 2, further comprising:
   controlling the first three-way control valve to fluidly couple the first test conduit to the bypass conduit while fluidly isolating the first test conduit from the second test conduit;
   controlling a two-way valve to fluidly couple the bypass conduit to an outlet of the biocide testing system; and
   circulating the first biocide out of the first test conduit, through the bypass conduit, and through the outlet.

8. The method of claim 1, wherein determining the effectiveness of the first biocide based on the immersion of the first plurality of test coupons in the portion of the first biocide comprises calculating a bacterial growth rate over time of bacteria formed on the first plurality of test coupons over the first time duration.

9. The method of claim 1, wherein controlling the first three-way control valve comprises commanding, with a control system communicably coupled to a first valve actuator coupled to the first three-way control valve, the first valve actuator to adjust the first three-way control valve to fluidly couple the source of water to the first test conduit.

10. A method for testing one or more biocides, comprising:
    controlling a first three-way control valve to fluidly couple a source of water to a first test conduit of a first test column of a biocide testing system;

circulating a flow of the water into a first inner volume of the first test conduit;

immersing a first plurality of test coupons positioned in the first inner volume in at least a portion of the flow of water;

fluidly coupling the first test conduit with a second test conduit of a second test column of the biocide testing system by opening a second three-way control valve coupled to a first loop conduit that is coupled between the first test conduit and the second test conduit;

circulating the flow of the water into a second inner volume of the second test conduit;

immersing a second plurality of test coupons positioned in the second inner volume in at least another portion of the flow of water;

controlling the second three-way control valve to fluidly isolate the first test column from the second test column;

after a first time duration:
 fluidly coupling a source of a first biocide to the first test conduit by opening the first three-way control valve,
 circulating a flow of the first biocide into the first inner volume of the first test conduit,
 immersing the first plurality of test coupons positioned in the first inner volume in at least a portion of the first biocide, and
 determining an effectiveness of the first biocide based on the immersion of the first plurality of test coupons in the portion of the first biocide; and after a second time duration:
 fluidly coupling a source of a second biocide to the second test conduit through a bypass conduit by opening the second three-way control valve;
 circulating a flow of the second biocide into the second inner volume of the second test conduit;
 immersing the second plurality of test coupons positioned in the second inner volume in at least a portion of the second biocide; and
 determining an effectiveness of the second biocide based on the immersion of the second plurality of test coupons in the portion of the second biocide, wherein a start time of the second time duration is coincident with a start time of the first time duration, and an end time of the second time duration is subsequent in time to an end time of the first time duration.

11. The method of claim 10, further comprising:
fluidly coupling the second test conduit with a third test conduit of a third test column of the biocide testing system by opening a third three-way control valve coupled to a second loop conduit that is coupled between the second test conduit and the third test conduit;

circulating the flow of the water into a third inner volume of the third test conduit;

immersing a third plurality of test coupons positioned in the third inner volume in at least another portion of the flow of water;

fluidly isolating the first and second test columns from the third test column by closing the third three-way control valve; and after a third time duration:
 fluidly coupling a source of a third biocide to the third test conduit through the bypass conduit by opening the third three-way control valve,
 circulating a flow of the third biocide into the third inner volume of the third test conduit,
 immersing the third plurality of test coupons positioned in the third inner volume in at least a portion of the third biocide, and
 determining an effectiveness of the third biocide based on the immersion of the third plurality of test coupons in the portion of the third biocide.

12. The method of claim 11, wherein each of the first, second, and third biocides comprises a different biocide.

13. The method of claim 11, wherein each start time of the first, second, and third time durations is coincident, and an end time of the third time duration is subsequent in time to an end time of the second time duration.

14. The method of claim 10, further comprising:
controlling the first three-way control valve to fluidly couple the first test conduit to the bypass conduit while fluidly isolating the first test conduit from the second test conduit;

controlling a two-way valve to fluidly couple the bypass conduit to an outlet of the biocide testing system; and circulating the first biocide out of the first test conduit, through the bypass conduit, and through the outlet.

15. The method of claim 10, wherein determining the effectiveness of the first biocide based on the immersion of the first plurality of test coupons in the portion of the first biocide comprises calculating a bacterial growth rate over time of bacteria formed on the first plurality of test coupons over the first time duration.

16. The method of claim 10, wherein controlling the first three-way control valve comprises commanding, with a control system communicably coupled to a first valve actuator coupled to the first three-way control valve, the first valve actuator to adjust the first three-way control valve to fluidly couple the source of water to the first test conduit.

17. A method for testing one or more biocides, comprising:
controlling a first three-way control valve to fluidly couple a source of water to a first test conduit of a first test column of a biocide testing system;

circulating a flow of the water into a first inner volume of the first test conduit;

immersing a first plurality of test coupons positioned in the first inner volume in at least a portion of the flow of water;

fluidly coupling the first test conduit with a second test conduit of a second test column of the biocide testing system by opening a second three-way control valve coupled to a first loop conduit that is coupled between the first test conduit and the second test conduit;

circulating the flow of the water into a second inner volume of the second test conduit;

immersing a second plurality of test coupons positioned in the second inner volume in at least another portion of the flow of water;

controlling the second three-way control valve to fluidly isolate the first test column from the second test column;

after a first time duration:
 fluidly coupling a source of a first biocide to the first test conduit by opening the first three-way control valve,
 circulating a flow of the first biocide into the first inner volume of the first test conduit,
 immersing the first plurality of test coupons positioned in the first inner volume in at least a portion of the first biocide, and determining an effectiveness of the first biocide based on the immersion of the first plurality of test coupons in the portion of the first biocide;

after a second time duration:
- fluidly coupling a source of a second biocide to the second test conduit through a bypass conduit by opening the second three-way control valve;
- circulating a flow of the second biocide into the second inner volume of the second test conduit;
- immersing the second plurality of test coupons positioned in the second inner volume in at least a portion of the second biocide; and
- determining an effectiveness of the second biocide based on the immersion of the second plurality of test coupons in the portion of the second biocide;

fluidly coupling the second test conduit with a third test conduit of a third test column of the biocide testing system by opening a third three-way control valve coupled to a second loop conduit that is coupled between the second test conduit and the third test conduit;

circulating the flow of the water into a third inner volume of the third test conduit;

immersing a third plurality of test coupons positioned in the third inner volume in at least another portion of the flow of water;

fluidly isolating the first and second test columns from the third test column by closing the third three-way control valve; and after a third time duration:
- fluidly coupling a source of a third biocide to the third test conduit through the bypass conduit by opening the third three-way control valve,
- circulating a flow of the third biocide into the third inner volume of the third test conduit,
- immersing the third plurality of test coupons positioned in the third inner volume in at least a portion of the third biocide, and
- determining an effectiveness of the third biocide based on the immersion of the third plurality of test coupons in the portion of the third biocide, wherein each start time of the first, second, and third time durations is coincident, and an end time of the third time duration is subsequent in time to an end time of the second time duration, and the end time of the second time duration is subsequent in time to an end time of the first time duration.

18. The method of claim 17, wherein each of the first, second, and third biocides comprises a different biocide.

19. The method of claim 17, further comprising:
controlling the first three-way control valve to fluidly couple the first test conduit to the bypass conduit while fluidly isolating the first test conduit from the second test conduit;
controlling a two-way valve to fluidly couple the bypass conduit to an outlet of the biocide testing system; and
circulating the first biocide out of the first test conduit, through the bypass conduit, and through the outlet.

20. The method of claim 17, wherein determining the effectiveness of the first biocide based on the immersion of the first plurality of test coupons in the portion of the first biocide comprises calculating a bacterial growth rate over time of bacteria formed on the first plurality of test coupons over the first time duration.

21. The method of claim 17, wherein controlling the first three-way control valve comprises commanding, with a control system communicably coupled to a first valve actuator coupled to the first three-way control valve, the first valve actuator to adjust the first three-way control valve to fluidly couple the source of water to the first test conduit.

* * * * *